United States Patent [19]

Hirsbrunner et al.

[11] 3,979,449

[45] Sept. 7, 1976

[54] PREPARATION OF AN ASPARAGINE OR A GLUTAMINE

[75] Inventors: Pierre Hirsbrunner, Corseaux; Raymond Bertholet, Aigle, both of Switzerland

[73] Assignee: Societe d'Assistance Technique pour Produits Nestle S.A., Lausaunne, Switzerland

[22] Filed: June 19, 1975

[21] Appl. No.: 588,181

[30] Foreign Application Priority Data

July 11, 1974 Switzerland............... 9572/74
Sept. 18, 1974 Switzerland............... 12673/74

[52] U.S. Cl................ 260/534 E; 260/534 G
[51] Int. Cl.²............................ C07C 99/00
[58] Field of Search............... 260/534 E, 534 G

[56] References Cited
UNITED STATES PATENTS

| | | | |
|---|---|---|---|
| 2,798,092 | 7/1957 | Joyce et al.............. | 260/534 G |
| 2,883,399 | 4/1959 | Amiard et al........... | 260/534 G |
| 3,105,852 | 10/1963 | Boissonnas............. | 260/534 G |

*Primary Examiner*—Joseph E. Evans
*Attorney, Agent, or Firm*—Kenyon & Kenyon Reilly Carr & Chapin

[57] ABSTRACT

A process for the preparation of compounds of the general formula

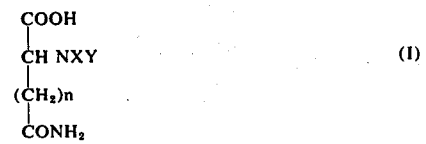 (I)

(in which $n$ is an integer equal to 1 or 2 and X and Y which may be the same or different are hydrogen atoms or organic groups, except that when $n=2$ not more than one of X and Y may represent a hydrogen atom) in which a compound of the general formula

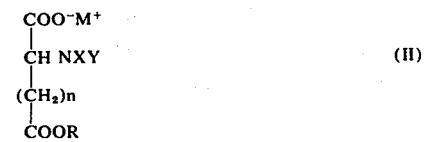 (II)

(in which $M^+$ represents a cation, R represents an aliphatic group containing 1 to 3 carbon atoms and X, Y and $n$ have the meanings given above) is reacted with ammonia in an aqueous medium and thereafter the compound of formula (I) is liberated by acidification of the reaction medium.

11 Claims, No Drawings

PREPARATION OF AN ASPARAGINE OR A GLUTAMINE

This invention relates to a process for the preparation of an asparagine or a glutamine with the exception of glutamine itself.

Asparagine and glutamine, which are amides with the developed formula (I, X=Y=H, n=1, n=2 respectively)

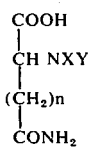

exist in two enantiomorphic forms D and L as a result of the presence of an asymmetric centre in the 2-position on the carbon atom carrying the amino group.

The synthesis of L-asparagine by treating β-methyl-L-aspartate with an alcoholic solution of ammonia gas is described in the Article by A. F. Beecham in J. Am. Chem. Soc. 76, 4615(1954). Unfortunately, this treatment has to be continued for about 2 days in order to obtain acceptable yields.

The synthesis of an L-glutamine derivative, α-(N-acetyl)-L-glutamine, by treating γ-methyl-α-(N-acetyl)-L-glutamate with an alcoholic solution of ammonia gas, is described in the Article by I. J. Maschler and N. Lichtenstein in Biochem. Biophys. Acta 57, 252 (1962). Unfortunately, this treatment has to be continued for 7 to 9 days at 37°C in order to obtain acceptable yields.

The present invention relates to a process which, in contrast to known processes, enables an asparagine or a glutamine, that is a compound corresponding to formula (I), with the exception of glutamine itself, to be obtained in high yields in only a few hours. The process according to the invention is distinguished by the fact that a compound corresponding to formula (II)

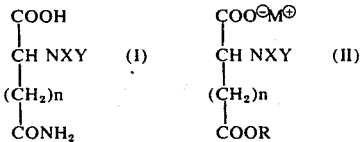

in which n is an integer equal to 1 or 2, $M^{\oplus}$ is a cation, X and Y are any substituents, except in cases where n=2 when they cannot both be hydrogen atoms, and R represents an aliphatic group with 1 to 3 carbon atoms, is reacted with ammonia in aqueous medium and the compound corresponding to formula (II) subsequently liberated by acidification of the reaction medium.

In other words, the invention relates to a process for the preparation of an asparagine (n=1) or of a glutamine (n=2), with the exception of glutamine itself (n=2, X=Y=H).

In the absence of a precise indication as to configuration, namely the letter D or L, the chemical designations used hereinafter apply to any of the enantiomers or to mixtures thereof, for example a racemic mixture, because the chemical process involved is not influenced by the chirality of the molecule.

The ester of an aspartic acid is an ester in the β-position of an aspartic acid, in other words an aspartic acid β-ester.

The ester of a glutamic acid, except for glutamic acid itself, is an ester in the γ-position of a glutamic acid, in other words a glutamic acid γ-ester.

The salt of the ester of formula (II) may be any soluble salt, for example the ammonium salt, the alkali or alkaline earth metal salts, etc. It is preferred to use the ammonium salt which, if desired, may be formed in situ by ammonia during the conversion of the ester into the amide from a solution or suspension of the corresponding free acid.

The substituents X and Y may be any substituents with the proviso that, being relatively remote from the reaction site, they are unable to interfere with the reaction. However, these two substituents cannot both be hydrogen atoms where n=2, because the treatment of an ester of glutamic acid with ammonia in aqueous medium does not give the glutamine, but a cyclisation product instead. X and Y are preferably hydrogen atoms (except if n=2) or akyl or acyl substituents having from 1 to 6 carbon atoms.

Thus, where X=Y=H, n=1 or where X or Y ≠ H, n=1 or 2, it is possible by the process according to the invention to produce asparagine itself, an N-substituted derivative of asparagine or of glutamine, for example α-(N-acetyl)-asparagine or α-(N-acetyl)-glutamine.

The main parameters capable of influencing the reaction process are the reaction time and the reaction temperature and the relative quantities of reactants used and the concentration of the aqueous ammoniacal medium.

The temperature at which the reaction is carried out is the result of a compromise. Thus, although an increase in the reaction temperature is a favourable factor because it increases the reaction velocity, it considerably reduces the quantity of ammonia which can be dissolved in the aqueous medium under a given pressure, i.e. the concentration of the aqueous ammoniacal medium. Thus, for example, the most favourable compromise at atmospheric pressure corresponds to the temperature range from 0° to 40°C, the reaction preferably being carried out at around ambient temperature. The reaction time is governed to some extent by the reaction temperature although, in practice, a reaction time of from 2 to 8 hours will be sufficient to form substantial quantities of the end product. Finally, rather than using the stoichiometric quantity of 1 mole of ammonia per mole of ester, an excess of ammonia is used, for example of 3 to 15 moles of ammonia per mole of ester.

The medium may be acidified with any acid, for example with hydrochloric acid or sulphuric acid, which enables the pH-value to be adequately reduced, i.e. to a pH-value of the order of 5.4 in the case of asparagine proper (isoelectric point) or to a pH-value below 4, preferably 2.5, in the case of N-substituted asparagines and glutamines. In addition, it is possible to remove the excess ammonia before acidification which may be accomplished very simply by evaporation in a partial vacuum or by bubbling through air or an inert gas, the ammonia recovered advantageously being recycled. Under the effect of acidification, the reaction product precipitates and may readily be recovered by filtration. After washing and drying, an asparagine or a glutamine with a purity of the order of 99% is obtained. If this purity is not high enough, the asparagine or glutamine may be recrystallised from water.

In one preferred embodiment of the process according to the invention, asparagine, one of its N-substituted derivatives or one of the N-substituted derivatives of glutamine is prepared from the ammonium salt of the corresponding methyl or ethyl ester.

In a first variant of this preferred embodiment, L-asparagine is prepared, being recovered in monohydrate form from the acidified reaction medium following the addition of methanol (in order to reduce the solubility of the L-asparagine).

In a second variant of this preferred embodiment, α-(N-acetyl)-L-asparagine is prepared and, if desired, may be hydrolysed into L-asparagine.

In a third variant of this preferred embodiment, α-(N-acetyl)-L-glutamine is prepared and, if desired, may be hydrolysed into L-glutamine.

In these last two cases, the starting material, namely the salt of an α-(N-acetyl)-L-aspartic acid β-ester or of an α-(N-acetyl)-L-glutamique acid γ-ester, may with advantage be prepared by acetylating with acetic anhydride the corresponding aspartic acid β-ester or glutamic acid γ-ester dissolved in an alcohol, for example methanol, or in a water-alcohol mixture, and converting the acetylated derivative into a salt by neutralisation to a pH-value of from 7 to 8.5. However, before being used as starting material, the solution containing this salt is preferably freed from the alcohol present, for example by evaporation under reduced pressure. The same procedure may of course be adopted for the D-derivatives.

The process according to the invention is illustrated in the following Examples, in which the percentages quoted represent percent by weight.

EXAMPLE 1

18.3 g of β-methyl-L-aspartate hydrochloride are dissolved in 80 ml of a solution containing 20 g of ammonia. After reaction at ambient temperature for 3 hours, during which the reaction mixture is slowly stirred, the excess ammonia is removed under a partial vacuum of 12 mm Hg. The pH-value is then reduced to pH 5.4 by the addition of 10 g of 32% hydrochloric acid. The L-asparagine is precipitated in monohydrate form. 200 g of methanol are then added to the mixture, followed by cooling to 0°C. The crystals are collected by filtration, washed with 20ml of a saturated (approximately 2%) aqueous solution of L-asparagine and then dried at 70°C. L-asparagine monohydrate is thus obtained in a yield of 12 g (80%). The product has the following characteristics:
  white crystalline powder;
  $[\alpha]_D^{20°C} = +34.1°$ ($c$=5; 6N HCL);
  m.p. = 235°C;
  single spot in thin-layer chromatography.

These characteristics correspond to a purity of at least 99%.

EXAMPLE 2

The procedure is as in Example 1 using 19.75 g of β-ethyl-L-aspartate hydrochloride. L-asparagine monohydrate is obtained in a yield of 10.5 g (70%), its characteristics being the same as the product of Example 1.

EXAMPLE 3

18.8 g of β-methyl-α-(N-acetyl)-L-aspartate are dissolved in 100 ml of a solution containing 25 g of ammonia. After reaction at ambient temperature for 5 hours, during which the reaction mixture is slowly stirred, the excess ammonia is removed under a partial vacuum of 12 mm Hg. The pH-value is then reduced to 2.5 by the addition of 10 g of 50% sulphuric acid, resulting in the precipitation of α-(N-acetyl)-L-asparagine. The mixture is cooled to 0°C and the crystals collected by filtration. The crystals are washed with 20 ml of methanol and then dried at 70°C. α-(N-acetyl)-L-asparagine is thus obtained in a yield of 8 g (45%). The product has the following characteristics:
  white crystalline powder;
  $[\alpha]_D^{20°C} = -1.5°$ ($c$=2; H$_2$O);
  m.p. = 160°C;
  single spot in thin-layer chromatography.

These characteristics correspond to a purity of at least 99%.

EXAMPLE 4

10 g of γ-methyl-L-glutamate are dissolved in 70 ml of methanol and 30 ml of water, followed by the addition of 10 ml of acetic anhydride. After reaction at 25°C for 2 hours, during which the reaction mixture is stirred, the pH-value of the medium is increased to pH 8 by the addition of 10 ml of concentrated ammonia. The methanol is then removed by evaporation under a partial vacuum of 50 mm Hg and at a temperature of 30°C, and 10 g of ammonia gas are dissolved in this solution, freed from methanol, by controlled bubbling through under atmospheric pressure. After stirring for 5 hours at 25°C, the excess ammonia is removed at 30°C under a partial vacuum of 50 mm Hg. The pH-value is then reduced to 2.5 by the addition of 12 ml of 50% sulphuric acid, resulting in the precipitation of α-(N-acetyl)-L-glutamine. The α-(N-acetyl)-L-glutamine is then collected by filtration, washed three times with 10 ml of cold water and then ovendried. 10 g of product (yield 85%) with the following characteristics are thus obtained:
  white crystalline powder;
  moisture content 0.5% — ash content 0.01%;
  $[\alpha]_D^{20°C} = -12.2°$ ($c$=3; H$_2$O);
  m.p. = 194.5°C;
  single spot in thin-layer chromatography.

These characteristics correspond to a purity of at least 99%.

EXAMPLE 5

The procedure is as in Example 4 using 10 g of γ-ethyl-L-glutamate dissolved in 70 ml of ethanol and 30 ml of water. α-(N-acetyl)-L-glutamine, with the same characteristics as the product of Example 1, is obtained in a yield of 6.5 g (60%).

The yield obtained is the same when the pH value is reduced to 2.5 by the addition of hydrochloric acid instead of sulphuric acid.

We claim:

1. A process for the preparation of compounds of the general formula

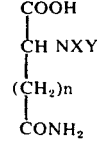

(1)

(in which $n$ is an integer equal to 1 or 2 and X and Y which may be the same or different are hydrogen atoms or organic groups, except that when $n=2$ not more than one of X and Y may represent a hydrogen atom) in which a compound of the general formula

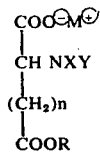

(II)

(in which $M^{\oplus}$ represents a cation, R represents an aliphatic group containing 1 to 3 carbon atoms and X, Y and $n$ have the meanings given above) is reacted with ammonia in an aqueous medium and thereafter the compound of formula (I) is liberated by acidification of the reaction medium.

2. A process as claimed in claim 1 which comprises reacting a compound of the general formula (II) in which X and Y, which may be the same or different, are alkyl or acyl groups containing 1 to 6 carbon atoms.

3. A process as claimed in claim 1 which comprises reacting a compound of the general formula (II) in which $n=1$ and X and Y are both hydrogen atoms.

4. A process as claimed in claim 3 in which the reaction medium is acidified to a pH of about 5.4.

5. A process as claimed in claim 1 which comprises reacting a compound of the general formula (II) in which X is a hydrogen atom and Y an acetyl group.

6. A process as claimed in claim 5 in which the reaction medium is acidified to a pH of about 2.5.

7. A process as claimed in claim 5 in which the compound of the general formula (II) used as starting material is prepared by acetylating a compound of the general formula (II) in which X and Y are both hydrogen atoms and the resulting acetylated derivative is converted into a salt by neutralisation to a pH-value of 7.0 to 8.5.

8. A process as claimed in claim 7 in which the acetylation is carried out in an alcoholic or aqueous-alcoholic medium.

9. A process as claimed in claim 1 which comprises reacting the L-form of a compound of the general formula (II) in which R represents a methyl or ethyl group.

10. A process as claimed in claim 1 which comprises reacting a compound of the general formula (II) in which $M^+$ is ammonium.

11. A process as claimed in claim 1 in which the reaction is effected at atmospheric pressure at a temperature not exceeding 40°C.

* * * * *